United States Patent [19]

Gunawardana et al.

[11] Patent Number: 5,182,287
[45] Date of Patent: Jan. 26, 1993

[54] BIOACTIVE HETEROCYCLE ALKALOIDS AND METHODS OF USE

[75] Inventors: Geewananda P. Gunawardana, Libertyville, Ill.; Peter J. McCarthy, Vero Beach, Fla.; Neal S. Burres, Libertyville, Ill.

[73] Assignee: Harbor Branch Oceanographic, Fort Pierce, Fla.

[21] Appl. No.: 747,560

[22] Filed: Aug. 20, 1991

Related U.S. Application Data

[63] Continuation-in-part of Ser. No. 431,260, Nov. 3, 1989, abandoned.

[51] Int. Cl.$^5$ .............. A61K 31/505; C07D 471/12; C07D 471/14; C07D 471/16
[52] U.S. Cl. ................................. 514/260; 546/48
[58] Field of Search ...................... 546/48; 514/260

[56] References Cited

U.S. PATENT DOCUMENTS

| | | | |
|---|---|---|---|
| 4,548,914 | 10/1985 | Rinehart, Jr. | 424/95 |
| 4,729,996 | 3/1988 | Wright et al. | 514/215 |
| 4,737,510 | 4/1988 | Rinehart, Jr. | 514/388 |
| 4,808,590 | 2/1989 | Higa et al. | 514/272 |

OTHER PUBLICATIONS

Schmitz et al., Pure and Applied Chem, vol. 62 (7) pp. 1393-1396 (1990).
Faulkner, D. J. (1984) "Marine Natural Products: Metabolites of Marine Invertebrates," Natural Products Reports 1:551-598.
Faulkner, D. J. (1985) "Marine Natural Products," Natural Products Reports 3:1-33.
Faulkner, D. J. (1987) "Marine Natural Products," Natural Products Reports 4:539-576.
Uemura, D. D. Takahashi, T. Yamamoto, C. Katayama, J. Tanaka, Y. Okumura, Y. Hirata (1985) "Norhalichondrin A: An Antitumor Polyether Macrolide from a Marine Sponge," J. Am. Chem. Soc. 107:4896-4798.
Kobayashi, J., J.-f. Cheng, H. Nakamura, Y. Ohizumi, Y. Hirata, T. Sasaki, T. Ohta, S. Nozoe (1988) "Ascididemnin, a novel pentacyclic aromatic alkaloid with potent antileukemic activity from the Okinawan tunicate Didemnin sp.," Tetrahedron Lett. 29(10):1177-1180.
Bloor, S. J., F. J. Schmitz (1987) "A Novel Pentacyclic Aromatic Alkaloid from an Ascidian," J. Am. Chem. Soc. 109:6134-6136.
de Guzman, F. S., F. J. Schmitz (1989) "Chemistry of 2-bromoleptoclinidinone, structure revision," Tetrahedron Lett. 30(9):1069-1070.
Schmitz, F. J., F. S. DeGuzman, M. B. Hossain, D. van der Helm (1991) "Cytotoxic Aromatic Alkaloids from the Ascidian Amphicarpa meridiana and Leptoclinides sp.: Meridine and 11-Hydroxyascididemnin," J. Org. Chem. 56:804-808.

Primary Examiner—Nicholas S. Rizzo
Assistant Examiner—Matthew Grumbling
Attorney, Agent, or Firm—Saliwanchik & Saliwanchik

[57] ABSTRACT

Novel heterocyclic alkaloids were isolated from a marine sponge. These compounds, and derivatives thereof, are useful antifungal and antitumor compounds. The novel compounds have the following structures:

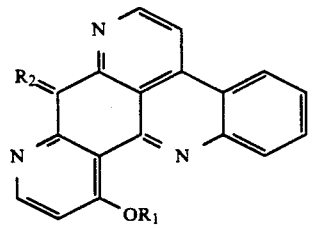

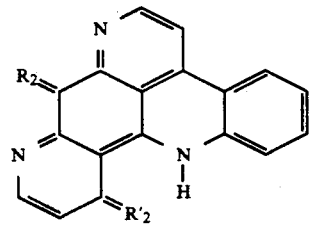

wherein
$R_1$ = H, alkyl, alkenyl, aryl, benzyl, acyl, benzoyl, or alkali metal;
$R_2$ and $R'_2$ = O, S, NOX, or NNHX, wherein X is alkyl or aryl.

14 Claims, No Drawings

BIOACTIVE HETEROCYCLE ALKALOIDS AND METHODS OF USE

CROSS-REFERENCE TO A RELATED APPLICATION

This is a continuation-in-part of our co-pending application Ser. No. 07/431,260, filed Nov. 3, 1989, now abandoned.

BACKGROUND OF THE INVENTION

Considerable research and resources have been devoted to oncology and antitumor measures including chemotherapy. While certain methods and chemical compositions have been developed which aid in inhibiting, remitting, or controlling the growth of tumors, new methods and antitumor chemical compositions are needed. The prevention and control of fungi is also of considerable importance to man, and much research has been devoted to development of antifungal measures.

It has been found that some natural products and organisms are potential sources for chemical molecules having useful biological activity of great diversity. Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge Theonella sp.; and U.S. Pat. No. 4,737,510 discloses compounds, having antiviral and antibacterial properties, isolated from the Caribbean sponge *Agelas conifera*. Clearly, marine sponges have proved to be a source of biological compounds, and a number of publications have issued disclosing organic compounds derived from marine sponges, including Scheuer, P. J. (ed.) *Marine Natural Products, Chemical and Biological Perspectives*, Academic Press, New York, 1978-1983, Vol. I-V; Faulkner, D. J., (1984) Natural Products Reports 1:551-598; Natural Products Reports (1986) 3:1-33; Natural Products Reports (1987) 4:539-576; J. Am. Chem. Soc. (1985) 107:4796-4798.

The subject invention concerns novel heterocycle alkaloids. Heterocycle compounds of marine tunicate origin have previously been described in Kobayashi, J., J. Chang, Y. Ohizumi, Y. Hirata, T. Sasaki, T. Ohta and S. Nozoe (1988) Tetrahedron Letters 29:1177-1180. Other heterocycle compounds of marine ascidian origin have been described in Bloor, S., F. J. Schmitz (1987) J. Amer. Chem. Soc. 109:6134; and de Guzman, F. S., F. J. Schmitz (1989) Tetrahedron Letters 30:1069. The present invention, utilizing sponges as a source material has provided the art with a new class of biologically active compounds and new pharmaceutical compositions useful as antitumor and antifungal agents. Subsequent to the filing of our parent application describing the novel compounds and their biological activities claimed here, Schmitz et al. have also reported the isolation of these compounds from marine organisms (Schmitz, F. J., F. S. DeGuzman, M. Bilayet Hossain, D. van der Helm [1991] J. Org. Chem. 56:804-808).

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The subject invention concerns novel heterocycle alkaloids and methods for use of these compounds. Specifically exemplified herein is a compound referred to as Compound Ia, its isomer (Ib), and derivatives. Compound Ia was isolated from the marine sponge Corticium. This compound, as well as its derivatives, have antitumor and antifungal activity. Thus, this new class of compounds and their analogs could be used as antitumor and/or antifungal agents.

DETAILED DESCRIPTION OF THE INVENTION

The subject invention pertains to a novel chemical compound, as well as its isomer and derivatives, isolated from marine sponges. These compounds have been shown to possess antitumor and antifungal activity. Thus, the subject invention pertains to the compounds themselves, as well as pharmaceutical compositions containing these compounds. Also disclosed and claimed are methods for administering the novel compositions. The derivatives of these compounds can be produced by known procedures. The parent compound can be isolated from marine sponges as described below.

The isolation of the natural product was performed using solvent partition and centrifugal countercurrent chromatography. The final purification of the novel compound and separation of its isomers, if present, can be achieved using HPLC. The structure of this compound was determined mainly on the basis of its $^1$H and $^{13}$C NMR data. The deduced structures of Compound Ia and its isomer Ib are shown below.

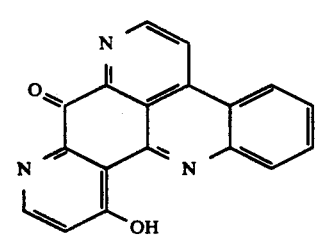

Ia

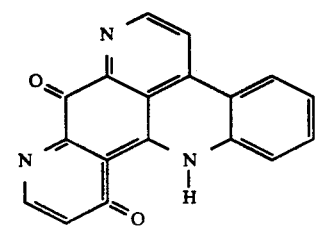

Ib

Various derivatives of compounds Ia and Ib can be prepared by procedures which are well known in the art. Examples of these derivatives are shown below and designated as IIa and IIb.

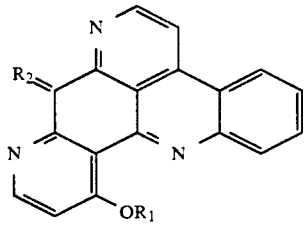

IIa

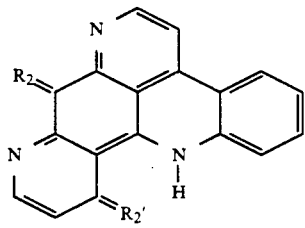

IIb $R_1$ = H, alkyl, alkenyl, aryl, benzyl, acyl, benzoyl, or alkali metal $R_2$ or $R'_2$ = O, S, NOX, or NNHX, wherein X is alkyl, aryl, or H The compounds of the subject invention, including derivatives thereof, have antitumor and antifungal properties. Thus, they can be used for the treatment of a number of diseases including cancer.

Following are examples which illustrate procedures, including the best mode, for practicing the invention. These examples should not be construed as limiting. All percentages are by weight and all solvent mixture proportions are by volume unless otherwise noted.

EXAMPLE 1

Identification and Location of Marine Sponge

The sponge of interest was collected by submersible southwest of Great Inagua Island, Bahamas, at latitude 20°54.04' North, and longitude 73°39.80' West at a depth of 450 feet. The sponge has been classified as follows:

Phylum: Porifera
Class: Demospongiae
Order: Homosclerophorida
Family: Plakinidae
Species: Corticium n. sp.

The sponge is a dark reddish-purple sponge encrusting on rubble. A taxonomic voucher specimen is deposited at the Harbor Branch Oceanographic Museum, Fort Pierce, Fla. (catalog number 003:00047).

EXAMPLE 2

Isolation of Compounds

The sponge collected in the Bahamas was kept frozen until workup. The organism was soaked in methanol for 2 hours, put through a blender, and exhaustively extracted with dichloromethane and dichloromethane methanol mixtures. The extracts were evaporated to dryness and separated by vacuum flash chromatography on RP $NH_2$ silica using solvent systems containing dichloromethane, methanol, and ammonia. The antifungal active fractions were combined and separated by centrifugal counter current chromatography using solvents consisting of methanol, water, dichloromethane, and ammonium hydroxide to give compound Ia. The fractions from vacuum flash chromatography also could be further purified by HPLC on RP $NH_2$ silica using dichloromethane, acetonitrile, methanol, water, ammonia solvent systems. If compound Ib is present, HPLC can be used to separate the isomers.

To confirm separation of the isomers and to identify them, the two isomers can be distinguished by nuclear overhouser enhancement (NOE) experiments on their hydrazone or oxime derivatives (IIa and IIb $R_2$=$NNH_2$ or $R_2$=NOH). In the NOE experiments, the irradiation of a proton, or of a set of protons under suitable conditions, results in changes in the intensity of the nuclear magnetic resonance (NMR) signals due to a proton or a set of protons which are located sufficiently close to the former proton(s). The magnitude of the intensity change is dependent upon the spatial proximity of the two types of protons concerned.

EXAMPLE 3

Characterization of Compound Ia

Compound Ia was isolated as a yellow solid sparingly soluble in organic solvents, but readily soluble in aqueous acids.

Mass Spectroscopy: Molecular Formula $C_{18}H_9N_3O_2$
High Resolution FAB Mass 302.0966, Δ3.7 mmu Proton NMR: $^1H$ ($CDCl_3$) 14.5 (1H, S, exchangeable, OH), 9.48 (1H, d, J=5 Hz, 2H), 8.75 (1H, d, 5.5 Hz, 3H), 8.65 (1H, d, J=5.6, 5 Hz, 12H), 8.62 (1H, d, J=8 Hz, 4H), 7.98 (1H, d, J=8 Hz, 7H), 7.96 (1H, dd, J=8, 7.5 Hz, 6H), 7.86 (1H, dd, J=8, 7.5 Hz, 5H), 7.25 (1H, d, J=5.6 Hz, 11H).

$^{13}C$ NMR: $^{13}C$ ($CDCl_3$) 180.3 (s), 167.2 (s), 153.7 (d), 151.5 (d), 49.4 (s), 148.4 (s), 147.5 (s), 142.4 (s), 137.8 (s), 132.6 (d), 129.6 (d), 129.3 (d), 123.3 (d), 121.7 (s), 119.7 (d), 117.6 (s), 116.9 (d), 116.4 (s).

EXAMPLE 4

Antifungal Properties

A. Protocol

1. Preparation of inocula

All media were autoclaved at 121° C. for 15 minutes.

*Candida albicans*: *C. albicans* (ATCC strain 44506) was grown on Sabouraud dextrose agar to produce single colonies, one of which was used to inoculate Sabouraud dextrose broth. The broth was incubated at 37° C. with shaking at 200 rpm for 18 hours. The resultant culture was brought to 10% (v/v) glycerol, frozen at −80° C., and used as the inoculum for the anti-Candida assay.

*Cryptococcus neoformans* (ATCC strain 32045) was prepared in a similar way using Emmon's modification of Sabouraud dextrose broth as the growth medium.

*Aspergillus nidulans*: *A. nidulans* (ATCC strain 36321) was grown from a spore stock on the surface of a YAG plate (YAG: yeast extract 0.5%; glucose 2%; agar 2%) at 30° C. until the colony sporulated; at this point the colony was green (usually within one week). Spores were harvested by washing with 0.1% (v/v) TRITON TM X-100. Spores were then washed with distilled water before freezing at −80° C. in the presence of 10% (v/v) glycerol.

Dermatophytic fungi: The strains in this panel were *Trichophyton mentagrophytes* (ATCC 9533), *Epidermophyton floccosum* (ATCC 52066), *Microsporum gypseum* (ATCC 42900), *M. canis* (ATCC 44459), *Scopulariopsis brevicaulis* (ATCC 36840), *Sporothrix schenkii* (ATCC 14284), and *Trichosporon beigelii* (ATCC 28592). These fungi were maintained as slants of Sabouraud dextrose agar and were subcultured every three months. Inocula for the assays were prepared by the maceration of the colony to produce a suspension of ~$10^3$ cfu/ml in sterile broth; this was used immediately in the agar dilution assay (see below).

*Bacillus subtilis*: Standard spore stocks (ATCC strain 6633) were purchased from Difco (#0453-36-0).

*Escherichia coli*: The BMR strain was used. This was grown overnight with shaking at 37° C. in nutrient broth and frozen in 1 mL aliquots in the presence of 10% (v/v) glycerol at −80° C.

*Pseudomonas aeruginosa*: (ATCC strain 27853) Grown and stored as described for *E. coli*.

2. Assay protocols i. Disc diffusion assay

*C. albicans* was inoculated into either melted Sabouraud dextrose agar or Roswell Park Memorial Institute medium 1640 (RPMI-1640) in 2% agar at 45° C. to give a cell density of approximately 10,000 cells/mL. Plates were prepared with 10 mL of the needed agar in a 10 cm × 10 cm petri dish. These plates were stored at 4° C. until needed for the assay.

*A. nidulans* spores were inoculated at 10,000/mL into melted YAG cooled to 45° C. Bacteria were inoculated into melted Penassay agar at a density of 10,000/ml. Plates were poured as described above.

Paper discs (6.35 mm) were impregnated with the test substance and allowed to dry. They were then placed onto the surface of a test plate prepared as detailed above. Plates were incubated overnight (*C. albicans, B. subtilis, E. coli*, and *P. aeruginosa* 37° C.; and *A. nidulans* 30° C.) after which time the zones of growth inhibition could be read. These are expressed as the diameter of the zone in millimeters. Standard drugs were used in all cases.

3. MIC protocol

Two-fold dilutions of the drug/extract were prepared in 50 μL volumes of a suitable solvent using 96-well microtiter plates. A 25% mixture of MeOH in water was generally used; however, EtOH, 5% EtOAc in EtOH, DMSO, or other compatible solvents could be substituted if necessary. In a separate 96-well plate, 35 μL volumes of either Sabouraud dextrose broth or RPMI-1640 were placed in each well. The drug/extract (5 μL) was then transferred to the broth using a 12-place pipettor. An inoculum of *C. albicans* in the appropriate medium was added to give a cell density of 1000 cells/mL and a total volume of 50 μL. If DMSO was used as solvent a total volume of 100 μL was used so that the DMSO level did not exceed 5%. SDB plates were incubated at 37° C. overnight, RPMI-1640 plates were incubated at 37° C. in a humidified atmosphere of 10% $CO_2$. 10 μL of triphenyl tetrazolium chloride (1% w/v; filter sterilized) was then added to each well; a further 2 hour incubation resulted in a deep coloration of the microorganism. The MIC is the lowest concentration of the drug which has completely inhibited growth.

4. Agar dilution assay (Dermatophytes)

Sabouraud dextrose agar was prepared and cooled to 45° C. Dilutions of the test compound were prepared in a suitable solvent and added to 5 mL agar to give the required concentration. The aliquots of agar were then poured into sections of a Quad-Petri dish. The agar was allowed to set at room temperature of 1-2 hours. Suspensions of dermatophytes were prepared as outlined above and were then aliquotted into the wells of a Steer's replicator. The organisms (1 μL) were then inoculated ont the surface of the agar. Plates were incubated at 28° C. for 4-7 days and were then scored for the growth of each colony type. The minimum inhibitory concentration was determined as the lowest concentration of the test compound which completely inhibited growth of the fungus. Terbinafin and miconazole were used as standard drugs for the assay.

5. Minimum fungicidal concentration (MFC)

MFC values were determined by an extension of the MIC method outlined above. MIC plates were prepared for *C. albicans* or *Cr. neoformans* and incubated as described. Triphenyl tetrazolium chloride was not added. The plates were mixed well to resuspend the cells. Two 20 μL aliquots were removed from each of the wells in which no growth was observed and were spread on the surface of Sabouraud dextrose agar plates. These plates were incubated for 18 hours at 37° C., at which time yeast colonies were counted. The MFC was defined as the lowest drug concentration resulting in a 99.9% killing of the inoculum.

B. Results

Compound Ia inhibits the growth of fungi such as *Candida albicans*. The antifungal activity may be of use in the treatment of fungal diseases of humans, animals, and possibly plants. Formulations may be for either topical or systemic use.

Compound Ia was tested for activity against a variety of microorganisms. Activities of the pure compound were as follows:

| Zones of inhibition | |
|---|---|
| *Candida albicans* (Sabouraud dextrose agar) | 8 mm |
| *Candida albicans* (RPMI-1640) | 14 mm |
| *Aspergillus nidulans* | ND* |
| *Bacillus subtilis* | 12 mm |
| *Escherichia coli* | ND* |
| *Pseudomonas aeruginosa* | ND* |

*ND = not detectable

TABLE 1

| Antifungal activity of Compound Ia | | |
|---|---|---|
| | Minimum Inhibitory Concentration μg/mL | Minimum Fungicidal Concentration μg/mL |
| *Candida albicans* | 3.1 | 3.1 |
| *Candida albicans* (RPMI) | 0.2 | 0.2 |
| *Cryptococcus neoformans* | 0.8 | 6.2 |
| *Epidermophyton floccosum* | 1.6 | NT |
| *Trichophyton mentagrophytes* | 6.2 | NT |

NT = Not Tested

EXAMPLE 5

P388 Mouse Leukemia Cell Assay

A. Maintenance of Cell Line

P388 murine leukemia cells obtained from Dr. J. Mayo, National Cancer Institute, Bethesda, MD, were maintained in Roswell Park Memorial Institute medium 1640 (RPMI-1640) supplemented with 10% horse serum and cultured in plastic tissue culture flasks and kept in an incubator at 37° C. in humidified air containing 5% $CO_2$. Antibiotic-free stock cultures of P388 cells were subcultured to $10^5$ cells/ml by dilutions in fresh growth medium at 2 to 5 day intervals.

B. Procedure

To assess the antiproliferative effects of agents against P388 cells, 200 μl cultures (96-well tissue culture plates, Nunc, Denmark) were established at 1×10⁵ cells/ml in drug-free medium containing agents at various concentrations. After 48 hour exposures, P388 cells were enumerated using 3-[4,5-dimethylthiazol-2-yl]-2,5-diphenyltetrazolium bromide (MTT) as described below.

To quantitate the effects of agents on cell proliferation, 75 μl warm growth medium containing 5 mg/ml MTT was added to each well. Cultures were returned to the incubator and left undisturbed for 90 minutes. To spectrophotometrically quantitate formation of reduced formazan, plates were centrifuged (900 g, 5 minutes), culture fluids were removed by aspiration, and 200 μl of acidified isopropanol (2 ml concentrated HCl/L isopropanol) added per well. The absorbance of the resulting solutions were measured at 570 mm with a plate reader (MR700 Microplate Reader, Dynatech Laboraties, Chantilly, VA). The absorbance of test wells was divided by the absorbance of drug free wells, and the concentration of the agent that resulted in 50% of the absorbance of untreated cultures was determined by linear regression of logit-transformed data. A linear relationship between P388 cell number and formazan production was found over the range of cell densities observed in this study.

C. Results

Compound Ia has strong inhibitory properties against mouse leukemia cells in vitro and has an IC$_{50}$ of 0.005 μg/ml compared to 0.1 μg/ml for the standard, 5-fluorouracil[50] used in this assay. The compound itself or a composition derived from it may provide a method for inhibiting tumors in humans or in animals.

EXAMPLE 6

Formulation and Administration

The compounds of the invention are useful for various non-therapeutic and therapeutic purposes. It is apparent from the testing that the compounds of the invention are effective for inhibiting fungal growth and for controlling tumor growth. Also, because of the antifungal properties of the compounds, they are useful to swab laboratory benches and equipment in a microbiology laboratory to eliminate the presence of fungi, or they can be used as ultraviolet screeners in the plastics industry since they effectively absorb UV rays. As disclosed herein, they are also useful prophylactically and therapeutically for treating fungal infections in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

We claim:

1. A compound having the following structure:

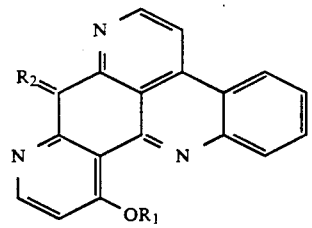

wherein R$_1$=H, alkyl, alkenyl, aryl, benzyl, acyl, benzoyl, or alkali metal; R$_2$=O, S, NOX, or NNHX, wherein X is alkyl or aryl.

2. The compound, according to claim 1, wherein R$_1$ is H and R$_2$ is O.

3. A compound having the following structure:

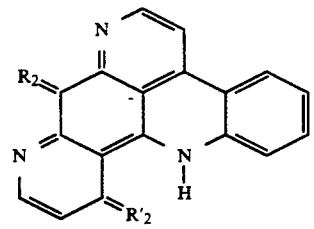

wherein R$_2$ and R'$_2$=O, S, NOX, or NNHX, wherein X is alkyl or aryl.

4. The compound, according to claim 3, wherein R$_2$ and R'$_2$ are O.

5. A process for inhibiting the growth of cancerous cells, said process comprising administering to said cells an effective cancerous cell inhibiting amount of a compound of claim 1 or 3.

6. The process, according to claim 5, wherein said compound is a compound of the formula:

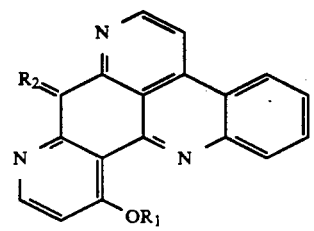

wherein R$_1$=H, alkyl, alkenyl, aryl, benzyl, acyl, benzoyl, or alkali metal; R$_2$=O, S, NOX, or NNHX, wherein X is alkyl or aryl.

7. The process, according to claim 5, wherein said compound is of the formula:

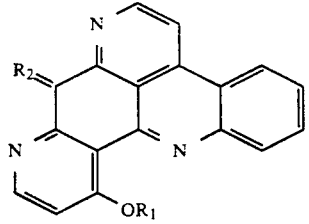

wherein $R_1$ is H and $R_2$ is O.

8. The process, according to claim 5, wherein said compound is a compound of the formula:

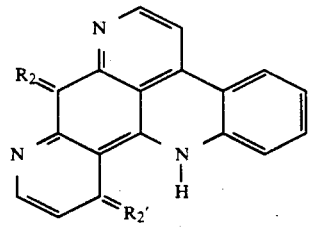

9. The process, according to claim 5, wherein said compound is a compound of the formula:

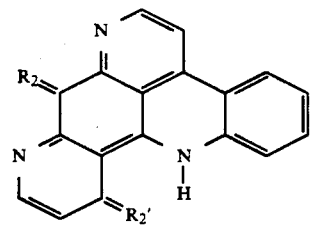

wherein $R_2$ and $R_2'$ are O.

10. A process for inhibiting fungal growth, said process comprising the administration of an effective fungal inhibiting amount of a compound of claim 1 or 3.

11. The process, according to claim 10, wherein said compound is a compound of the formula:

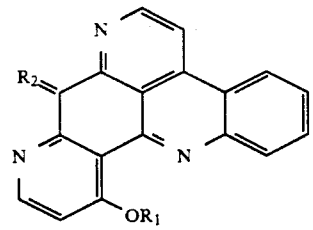

wherein $R_1$=H, alkyl, alkenyl, aryl, benzyl, benzoyl, or acyl, or alkali metal; $R_2$=O, S, NOX, or NNHX, wherein X is alkyl or aryl.

12. The process, according to claim 10, wherein said compound is a compound of the formula:

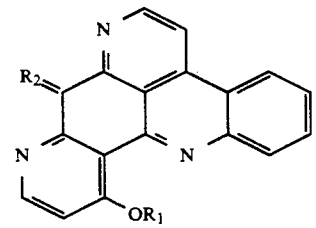

wherein R is H and $R_2$ is O.

13. The process, according to claim 10, wherein said compound is a compound of the formula:

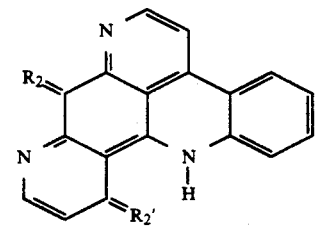

wherein $R_2$ and $R'_2$=O, S, NOX, or NNHX, wherein X is alkyl or aryl.

14. The process, according to claim 10, wherein said compound is a compound of the formula:

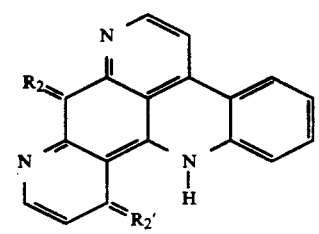

wherein $R_2$ and $R_2'$ are O.

* * * * *

UNITED STATES PATENT AND TRADEMARK OFFICE
CERTIFICATE OF CORRECTION

PATENT NO. : 5,182,287

DATED : January 26, 1993

INVENTOR(S) : Geewananda P. Gunawardana, et al

It is certified that error appears in the above-identified patent and that said Letters Patent is hereby corrected as shown below:

Column 2: structure Ib:

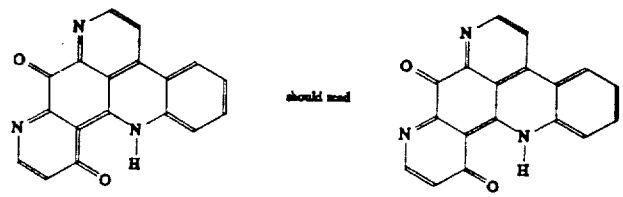

Column 4: line 32: "49.4" should read --149.4--.
Column 7: line 16: "570 mm" should read --570 nm--.
Column 10: line 29: "R is H" should read --$R_1$ is H--.

Signed and Sealed this

Seventh Day of December, 1993

Attest:

BRUCE LEHMAN

*Attesting Officer*  *Commissioner of Patents and Trademarks*